United States Patent
Hagiwara (10) Patent No.: US 8,576,981 B2
(45) Date of Patent: Nov. 5, 2013

(54) IMAGE RECONSTRUCTION METHOD AND X-RAY CT APPARATUS

(75) Inventor: Akira Hagiwara, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 863 days.

(21) Appl. No.: 12/652,711

(22) Filed: Jan. 5, 2010

(65) Prior Publication Data

US 2010/0172564 A1    Jul. 8, 2010

(30) Foreign Application Priority Data

Jan. 5, 2009    (JP) ................................ 2009-000140

(51) Int. Cl.
*A61B 6/03*    (2006.01)

(52) U.S. Cl.
USPC .................................. 378/15; 378/4; 382/131

(58) Field of Classification Search
USPC .................. 378/4, 15, 901; 382/131
See application file for complete search history.

(56) References Cited

U.S. PATENT DOCUMENTS

| | | | |
|---|---|---|---|
| 6,108,575 A | | 8/2000 | Besson |
| 6,341,154 B1 * | | 1/2002 | Besson ........................... 378/15 |
| 6,408,044 B2 * | | 6/2002 | Sembritzki et al. .............. 378/15 |
| 6,463,118 B2 | | 10/2002 | Besson |
| 6,744,844 B2 | | 6/2004 | Horiuchi |
| 6,795,522 B2 | | 9/2004 | Nishide et al. |
| 6,865,247 B2 * | | 3/2005 | Hagiwara ........................... 378/4 |
| 6,873,679 B2 * | | 3/2005 | Hagiwara ........................ 378/19 |
| 7,020,317 B2 * | | 3/2006 | Grass et al. .................... 382/131 |
| 7,173,997 B2 * | | 2/2007 | Hagiwara ........................ 378/15 |
| 7,260,175 B2 * | | 8/2007 | Hagiwara et al. ............... 378/19 |
| 7,269,244 B2 * | | 9/2007 | Tang et al. ....................... 378/19 |
| 7,324,622 B2 * | | 1/2008 | Morikawa et al. ................. 378/4 |
| 7,379,534 B2 | | 5/2008 | Hagiwara |
| 7,573,973 B2 * | | 8/2009 | Tang et al. ......................... 378/4 |
| 7,583,777 B2 * | | 9/2009 | Tang et al. ......................... 378/4 |
| 7,606,345 B2 * | | 10/2009 | Nishide et al. .................... 378/4 |
| 7,649,972 B2 * | | 1/2010 | Hagiwara et al. ................. 378/4 |

(Continued)

FOREIGN PATENT DOCUMENTS

| | | |
|---|---|---|
| JP | 05-091996 | 4/1993 |
| JP | 09-238935 | 9/1997 |

(Continued)

OTHER PUBLICATIONS

Tang et al., "A three-dimensional-weighted cone beam filtered backprojection (CB-FBP) algorithm for image reconstruction in volumetric CT—helical scanning," Phys. Med. Biol. 51 (2006), 855-874.*

Xiangyang Tang et al., A three-dimensional weighted cone beam filtered backprojection (CB-FBP) algorithm for image reconstruction in volumetric CT under a circular source trajectory, Phys. Med. Biol., 2005, pp. 3889-3905, 50.

Notice of Reasons for Rejection, Japanese Patent Office, Application No. 2009-000140 dated Mar. 6, 2013, pp. 2.

*Primary Examiner* — Allen C. Ho (74) *Attorney, Agent, or Firm* — Armstrong Teasdale LLP (57) ABSTRACT

An image reconstruction method includes a reconstruction algorithm of pixel data, weighting coefficients by which first projection data and second projection data at which a corresponding X-ray beam passes through a pixel lying on a reconstruction plane and which are opposite in view angle direction to each other, are to be multiplied, are calculated by equations each using a term of a distance between an X-ray generator and detector system and the reconstruction plane plus an offset distance at the acquisition of the projection data.

22 Claims, 9 Drawing Sheets

(56) References Cited

U.S. PATENT DOCUMENTS

| | | | |
|---|---|---|---|
| 7,831,011 B2 * | 11/2010 | Ayala et al. | 378/8 |
| 8,131,042 B2 * | 3/2012 | Tang et al. | 382/131 |
| 2009/0086888 A1 | 4/2009 | Hagiwara et al. | |

FOREIGN PATENT DOCUMENTS

| | | |
|---|---|---|
| JP | 2005-137392 | 6/2005 |
| JP | 2007-236662 A | 9/2007 |
| WO | 2004-034907 A1 | 4/2004 |

* cited by examiner

IMAGE RECONSTRUCTION METHOD AND X-RAY CT APPARATUS

CROSS REFERENCE TO RELATED APPLICATIONS

This application claims the benefit of Japanese Patent Application No. 2009-000140 filed Jan. 5, 2009, which is hereby incorporated by reference in its entirety.

BACKGROUND OF THE INVENTION

The embodiments described herein relate to an image reconstruction method and an X-ray CT (Computed Tomography) apparatus.

When a CT image is reconstructed based on projection data acquired by an X-ray CT scan, pixel data of each pixel on a reconstruction plane, corresponding to the CT image has heretofore been reconstructed using general formulas for backprojection arithmetic operation including weighting, such as expressed in the following equations (refer to, for example, "A three-dimensional weighted cone beam filtered backprojection (CB-FBP) algorithm for image reconstruction in volumetric CT under a circular source trajectory", Physics In Medicine And Biology, 50 (2005), P.3889-3905, Xiangyang Tang, Jiang Hsieh, Akira Hagiwara, et al.).

$$f(x, y, z) = \frac{\pi}{(\beta_{max} - \beta_{min})} \int_{\beta_{min}}^{\beta_{max}} \frac{Fi}{\sqrt{(Fi)^2 + Z^2}} \omega(\beta, \gamma) \tilde{s}(\alpha, \beta, \gamma) d\beta \quad (1)$$

$$\tilde{s}(\alpha, \beta, \gamma) = s(\alpha, \beta, \gamma) \otimes g(\gamma) \quad (2)$$

As shown above, $f(x, y, z)$ in equation (1) indicates pixel data of a pixel $P(x, y, z)$ on a reconstruction plane RP, $s(\alpha, \beta, \gamma)$ indicates projection data based on an X-ray beam that passes through the pixel $P(x, y, z)$ on the reconstruction plane RP, $g(\gamma)$ indicates a reconstruction function, a symbol $\otimes$ with X being surrounded with $\circ$ indicates a convolution operator, $\alpha$, indicates a cone angle formed as viewed from a plane that passes through an X-ray focal point F and a center line in a slice direction, of an X-ray detector D, $\beta$ indicates a view angle position on a circular orbit, of the X-ray focal point F, $\gamma$ indicates an angle in a channel direction as viewed from a central axis of a fan-beam X ray, Fi indicates the distance from the X-ray focal point F to a rotational center axis Ic of the X-ray focal point F, Z indicates a predetermined value that depends on a z coordinate of the pixel P, and $\omega(\beta, \gamma)$ indicates a weighting coefficient (weighting factor) by which the projection data $s(\alpha, \beta, \gamma)$ is multiplied. Incidentally, $(\beta_{max} - \beta_{min} = \pi + 2\gamma_m$ (where $\gamma_m$=half of a fan angle of a fan-shaped X-ray beam) in the case of half reconstruction, and $\beta_{max} - \beta_{min} = 2\pi$ or $2\pi + 2\gamma_m$ in the case of full reconstruction.

Incidentally, weighting coefficients by which plural projection data substantially identical or opposite to one another in view angle direction $\theta$, of the projection data $s(\alpha, \beta, \gamma)$ are multiplied are set so that the sum thereof reaches 1.

Now consider where the X-ray CT scan is taken as a helical scan. In this case, there can be considered as projection data $s(\alpha, \beta, \gamma)$, first projection data $s(\alpha di, \beta di, \gamma di)$ at which an angle direction at the time that a corresponding X-ray beam passes through a pixel P from one plane side of a reconstruction plane RP and is projected onto the reconstruction plane RP, is a view angle direction $\theta i$, and second projection data $s(\alpha ci, \beta ci, \gamma ci)$ at which an angle direction at the time that a corresponding X-ray beam passes through the pixel P from the other plane side of the reconstruction plane RP and is projected onto the reconstruction plane RP is a view angle direction opposite to the view angle direction $\theta i$. At this time, a weighting coefficient $\omega(\beta di, \gamma di)$ by which the first projection data $s(\alpha di, \beta di, \gamma di)$ is to be multiplied, and a weighting coefficient $\omega(\beta ci, \gamma ci)$ by which the second projection data $s(\alpha ci, \beta ci, \gamma ci)$ is to be multiplied, can be determined in accordance with, for example, the following equations:

$$\omega(\beta_d i, \gamma_d i) = \frac{\Delta Z_c i}{\Delta Z_c i + \Delta Z_d i}, \omega(\beta_c i, \gamma_c i) = \frac{\Delta Z_d i}{\Delta Z_c i + \Delta Z_d i} \quad (3)$$

$$\omega(\beta_d i, \gamma_d i) + \omega(\beta_c i, \gamma_c i) = 1 \quad (4)$$

In the equations, $\Delta Zdi$ indicates the distance in a z direction between a reference position (for example, a position of a point where a straight line formed by connecting an X-ray focal point F and the center of an X-ray detector 24 and a rotational axis Ic of an X-ray generator and detector system 41 intersect) of the X-ray generator and detector system at the time that the first projection data $s(\alpha di, \beta di, \gamma di)$ is acquired, and a reconstruction plane RP, and $\Delta Zci$ indicates the distance in the z direction between the reference position of the X-ray generator and detector system at the time that the second projection data $s(\alpha ci, \beta ci, \gamma ci)$ is acquired, and the reconstruction plane RP. Incidentally, the equation (4) is described in the sense of confirmation.

BRIEF DESCRIPTION OF THE INVENTION

Meanwhile, when both of the distances $\Delta Zdi$ and $\Delta Zci$ assume a small or minute value as in the case where a helical pitch at a helical scan is very small, etc., the X-ray beams X $(\alpha di, \beta di, \gamma di)$ and X $(\alpha ci, \beta ci, \gamma ci)$ are brought to ones that do not vary substantially positionally. Namely, both of these X-ray beams hardly deviate from the reconstruction plane RP. Such first and second projection data $s(\alpha di, \alpha di, \gamma di)$ and $s(\alpha ci, \beta ci, \gamma ci)$ based on the X-ray beams are both useful for reconstruction of pixel data, and an improvement in image quality can be expected if they are used in combination.

According to the equations for determining the weighting coefficients, however, when the distances $\Delta Zdi$ and $\Delta Zci$ both assume a minute value close to zero, and a large deviation occurs between the distances $\Delta Zdi$ and $\Delta Zci$ as a ratio, e.g. when $\Delta Zdi$=0.0001 mm or so and $\Delta Zci$=0.01 mm or so, a relatively large weighting coefficient is assigned to either one of projection data, and a relatively small weighting coefficient is assigned to the other thereof. Namely, although the two are both useful projection data, only one projection data substantially contributes to the reconstruction, and another projection data cannot be utilized without wastes.

With the foregoing in view, embodiments of the present invention provide an image reconstruction method and an X-ray CT apparatus that reliably use projection data based on an X-ray beam close to a reconstruction plane, of projection data acquired by a helical scan.

In a first aspect, the present invention provides an image reconstruction method for reconstructing a CT image using projection data acquired by a helical scan for performing each scan while relatively linearly moving an X-ray generator and detector system in a direction of a body axis of the subject, wherein said X-ray generator and detector system comprises an X-ray tube for applying X-rays and an X-ray detector having at least one detector row for detecting an X-ray transmitted through a subject, the method comprising the step of obtaining image data of the said CT image, using projection data lying in a view range including views each corresponding to a time at which a reconstruction plane of the CT image and a reference position of the X-ray generator and detector system coincide with each other in the body-axis direction, by performing a backprojection arithmetic operation including weighting based on a distance in the body-axis direction between the reconstruction plane and the reference position of the X-ray generator and detector system corresponding to the view for the projection data, wherein said weighting is performed based on a distance obtained by adding a positive predetermined value to said distance, in place of said distance.

In a second aspect, the present invention provides the image reconstruction method according to the first aspect, wherein weighting coefficients based on a ratio between distances added with the predetermined value at first projection data and second projection data are used for the weighting, the first projection data being based on an X-ray beam passing through a predetermined pixel on the reconstruction plane or its proximal position at a view when the reference position of the X-ray generator and detector system is placed on one plane side of the reconstruction plane, and the second projection data being based on an X-ray beam passing through the predetermined pixel or its proximal position in a view angle direction substantially identical or opposite to the first projection data at a view when the reference position of the X-ray generator and detector system is placed on the other plane side of the reconstruction plane.

Here, the projection data "based on the X-ray beam passing through the predetermined pixel or its proximal position" corresponds to projection data considered to effectively contribute to the reconstruction of pixel data of the predetermined pixel.

In a third aspect, the present invention provides the image reconstruction method according to the second aspect, wherein the weighting coefficient relative to the first projection data includes a term expressed in the following equation:

$$\frac{\Delta Z_c + \Delta Z_{offset}}{(\Delta Z_d + \Delta Z_{offset}) + (\Delta Z_c + \Delta Z_{offset})},$$

wherein the weighting coefficient relative to the second projection data includes a term expressed in the following equation:

$$\frac{\Delta Z_d + \Delta Z_{offset}}{(\Delta Z_d + \Delta Z_{offset}) + (\Delta Z_c + \Delta Z_{offset})},$$

and
wherein $\Delta Zc$ indicates the distance at the first projection data, $\Delta Zd$ indicates the distance at the second projection data, and $\Delta Zoffset$ indicates the predetermined value.

In a fourth aspect, the present invention provides the image reconstruction method according to the second or third aspect, wherein the X-ray beam passing through the predetermined pixel or its proximal position is parallel to the reconstruction plane.

In a fifth aspect, the present invention provides the image reconstruction method according to the second or third aspect, wherein the X-ray detector has a plurality of detector rows, and wherein the X-ray beam passing through the predetermined pixel or its proximal position passes through the reconstruction plane.

In a sixth aspect, the present invention provides the image reconstruction method according to any one of the first through fifth aspects, wherein the predetermined value becomes small as a helical pitch becomes large.

Here, the "helical pitch" corresponds to a value obtained by dividing a distance at which the X-ray generator and detector system relatively linearly moves while the X-ray generator and detector system rotates once, by a scan width (width on a rotational axis of the X-ray generator and detector system, of an X-ray beam radiated from the X-ray tube).

In a seventh aspect, the present invention provides the image reconstruction method according to the sixth aspect, wherein the predetermined value changes according to a helical pitch at a variable pitch helical scan at which the helical pitch changes while the helical scan is being performed.

In an eighth aspect, the present invention provides the image reconstruction method according to any one of the first through seventh aspects, wherein the backprojection arithmetic operation includes weighting of projection data acquired where the helical pitch is 0.5 or less.

In a ninth aspect, the present invention provides the image reconstruction method according to any one of the first through eighth aspects, wherein the predetermined value falls within a range from greater than or equal to d/100 to less than or equal to 30 d when a width obtained by dividing a width in the body-axis direction, of the X-ray beam radiated from the X-ray tube by the number of the detector rows is assumed to be d.

In a tenth aspect, the present invention provides the image reconstruction method according to any one of the first through ninth aspects, wherein the view range corresponds to a π+fan angle of the X-ray beam radiated from the X-ray tube, 2π, or a 2π+view angle of the fan angle.

In an eleventh aspect, the present invention provides the image reconstruction method according to any one of the first through tenth aspects, wherein the reference position of the X-ray generator and detector system corresponds to a position of a point where a straight line formed by connecting an X-ray focal point of the X-ray tube and the center of the X-ray detector, and a rotational axis of the X-ray generator and detector system intersect.

In a twelfth aspect, the present invention provides an X-ray CT apparatus comprising data acquiring device for acquiring projection data by a helical scan for performing each scan while relatively linearly moving an X-ray generator and detector system in a direction of a body axis of the subject, wherein said X-ray generator and detector system comprises an X-ray tube for applying X-rays and an X-ray detector having at least one detector row for detecting an X-ray transmitted through a subject and image reconstructing device for reconstructing a CT image using the acquired projection data, wherein the image reconstructing device is configured to obtain image data of the said CT image, using projection data lying in a view range including views each corresponding to a time at which a reconstruction plane of the CT image and a reference position of the X-ray generator and detector system coincide with each other in the body-axis direction, by performing a backprojection arithmetic operation including weighting based on a distance in the body-axis direction between the reconstruction plane and the reference position of the X-ray generator and detector system, corresponding to the view for the projection data, and wherein said weighting is performed based on a distance obtained by adding a positive predetermined value to said distance, in place of said distance.

In a thirteenth aspect, the present invention provides the X-ray CT apparatus according to the twelfth aspect, wherein the image reconstructing device uses, for the weighting, weighting coefficients based on a ratio between distances added with the predetermined value at first projection data and second projection data, the first projection data being based on an X-ray beam passing through a predetermined pixel on the reconstruction plane or its proximal position at a view taken when the reference position of the X-ray generator and detector system is placed on one plane side of the reconstruction plane, and the second projection data being based on an X-ray beam passing through the predetermined pixel or its proximal position in a view angle direction substantially identical or opposite to the first projection data at a view taken when the reference position of the X-ray generator and detector system is placed on the other plane side of the reconstruction plane.

In a fourteenth aspect, the present invention provides the X-ray CT apparatus according to the thirteenth aspect, wherein the weighting coefficient relative to the first projection data includes a term expressed in the following equation:

$$\frac{\Delta Z_c + \Delta Z_{offset}}{(\Delta Z_d + \Delta Z_{offset}) + (\Delta Z_c + \Delta Z_{offset})},$$

wherein the weighting coefficient relative to the second projection data includes a term expressed in the following equation:

$$\frac{\Delta Z_d + \Delta Z_{offset}}{(\Delta Z_d + \Delta Z_{offset}) + (\Delta Z_c + \Delta Z_{offset})},$$

and wherein $\Delta Z_c$ indicates the distance at the first projection data, $\Delta Z_d$ indicates the distance at the second projection data, and $\Delta Z_{offset}$ indicates the predetermined value.

In a fifteenth aspect, the present invention provides the X-ray CT apparatus according to the thirteenth or fourteenth aspect, wherein the X-ray beam passing through the predetermined pixel or its proximal position is parallel to the reconstruction plane.

In a sixteenth aspect, the present invention provides the X-ray CT apparatus according to the thirteenth or fourteenth aspect, wherein the X-ray detector has a plurality of detector rows, and wherein the X-ray beam passing through the predetermined pixel or its proximal position passes through the reconstruction plane.

In a seventeenth aspect, the present invention provides the X-ray CT apparatus according to any one of the twelfth through sixteenth aspects, wherein the predetermined value becomes small as a helical pitch becomes large.

In an eighteenth aspect, the present invention provides the X-ray CT apparatus according to the seventeenth aspect, wherein the predetermined value changes according to a helical pitch at a variable pitch helical scan at which the helical pitch changes while the helical scan is being performed.

In a nineteenth aspect, the present invention provides the X-ray CT apparatus according to any one of the twelfth through eighteenth aspects, wherein the backprojection arithmetic operation includes weighting of projection data acquired where the helical pitch is 0.5 or less.

In a twentieth aspect, the present invention provides the X-ray CT apparatus according to any one of the twelfth through nineteenth aspects, wherein the predetermined value falls within a range from greater than or equal to d/100 to less than or equal to 30 d when a width obtained by dividing a width in the body-axis direction, of the X-ray beam radiated from the X-ray tube by the number of the detector rows is assumed to be d.

In a twenty-first aspect, the present invention provides the X-ray CT apparatus according to any one of the twelfth through twentieth aspects, wherein the view range corresponds to a π+fan angle of the X-ray beam radiated from the X-ray tube, 2π, or a 2π+view angle of the fan angle.

In a twenty-second aspect, the present invention provides the X-ray CT apparatus according to any one of the twelfth through twenty-first aspects, wherein the reference position of the X-ray generator and detector system corresponds to a position of a point where a straight line formed by connecting an X-ray focal point of the X-ray tube and the center of the X-ray detector, and a rotational axis of the X-ray generator and detector system intersect.

According to the present invention, when a backprojection arithmetic operation including weighting based on a distance in the direction of a body axis of a subject between a reconstruction plane of each CT image and a reference position of an X-ray generator and detector system, corresponding to each of views for projection data is performed to thereby determine image data for the CT image, a distance obtained by adding a positive predetermined value to the above distance is used for the weighting as an alternative to the above distance. Therefore, even if any of the distances corresponding to the respective projection data assume a minute value, a state in which any one of weighting coefficients (weighting factors) becomes extremely small can be prevented owing to the existence of the predetermined value, and projection data based on an X-ray beam close to the reconstruction plane, of projection data acquired by a helical scan can reliably be utilized.

DETAILED DESCRIPTION OF THE INVENTION

Embodiments of the present invention will hereinafter be described in further detail in accordance with an embodiment illustrated in the accompanying drawings. Incidentally, the present invention is not limited to or by the embodiments described herein.

Figure 1:
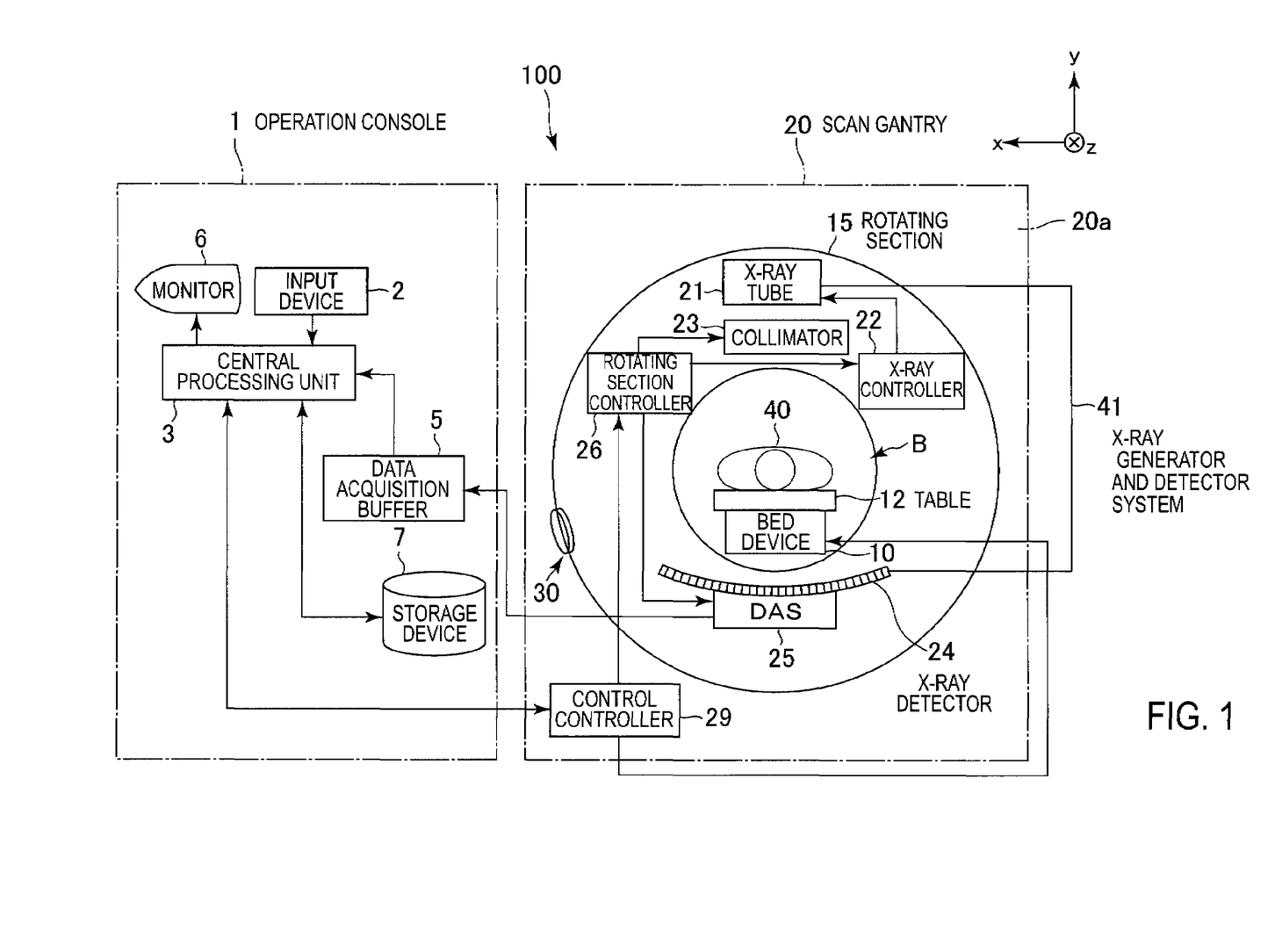
FIG. 1 is a configuration diagram showing an X-ray CT apparatus according to the present embodiment.

FIG. 1 is a configuration diagram showing an X-ray CT apparatus 100 according to the present embodiment.

The X-ray CT apparatus 100 is equipped with an operation console 1, a bed device 10, and a scan gantry 20.

The operation console 1 is equipped with an input device 2 which accepts an input from a user, a central processing unit 3 which executes control for data acquisition, processing of acquired data, etc., a data acquisition buffer 5 which acquires projection data acquired by the scan gantry 20, a monitor 6 which displays each reconstructed CT image, based on the projection data, and a storage device 7 which stores programs, image data about CT images, etc. therein.

The bed device 10 is equipped with a table 12 which places a subject 40 thereon and inserts and draws the subject 40 into and from a bore B of the scan gantry 20. The table 12 is elevated and linearly moved horizontally by a motor built in the bed device 10. Incidentally, in the present embodiment, the linear moving direction of the table 12 is assumed to be a z direction, its vertical direction is assumed to be a y direction, and its horizontal direction orthogonal to the z and y directions is assumed to be an x direction.

The scan gantry 20 has a rotating section 15 and a body section 20a which rotatably supports the rotating section 15. The rotating section 15 is equipped with an X-ray tube 21, an X-ray controller 22 which controls the X-ray tube 21, a collimator 23 which shapes an X-ray beam radiated from the X-ray tube 21, an X-ray detector 24 in which plural detector rows comprising plural X-ray detecting elements disposed in a channel direction are arranged in the z direction, a DAS (Data Acquisition System) 25 which converts outputs of the X-ray detector 24 to projection data and acquires them, and a rotating section controller 26 which controls the X-ray controller 22, collimator 23 and DAS 25. The X-ray tube 21 and the X-ray detector 24 configure an X-ray data acquisition system or an X-ray generator and detector system 41. The body section 20a is equipped with a control controller 29 which exchanges control signals or the like with the operation console 1 and the bed device 10. The rotating section 15 and the body section 20a are electrically coupled to each other via a slip ring 30.

Incidentally, the DAS 25 sends a view angle position 13 on a circular orbit of the X-ray tube 21 at the time that each projection data is acquired every view, and the position in the z direction of the table 12 to the data acquisition buffer 5, incident to the acquired projection data. It is thus possible to specify whether projection data corresponding to the respective detecting elements of the X-ray detector 24 depend on X-ray beams placed in any positional relationship in an imaging space.

Incidentally, the scan gantry 20 and the central processing unit 3 are illustrative of one example of X-ray data acquiring device according to the present invention. The central processing unit 3 is one example of image reconstructing device according to the present invention.

Figure 2:
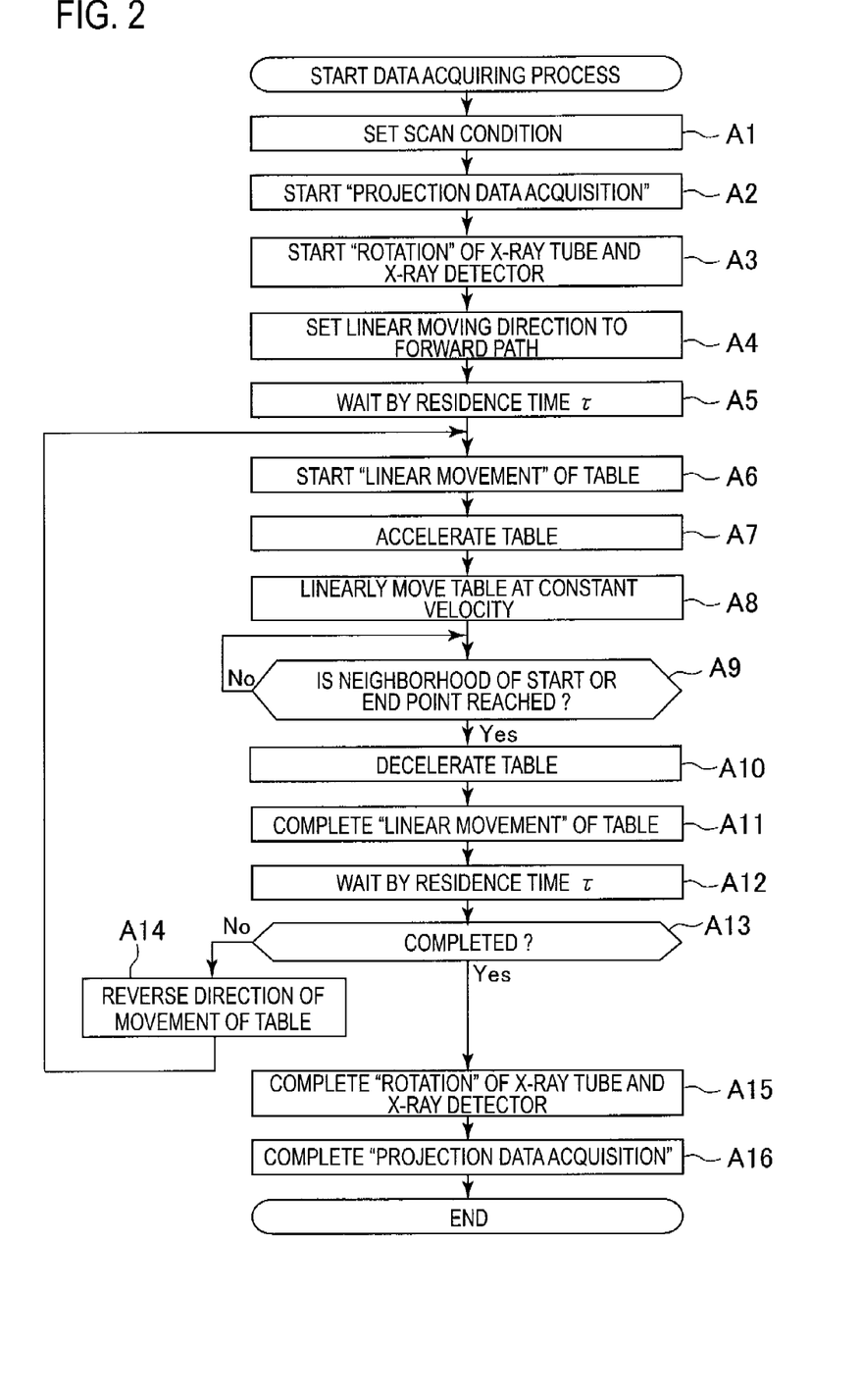
FIG. 2 is a flow diagram illustrating a data acquiring process according to the present embodiment.

FIG. 2 is a flow diagram showing a data acquiring process.

Here, projection data are acquired by a variable pitch helical scan. This scan corresponds to a helical scan for acquiring projection data even during a period in which a helical pitch changes. Here, the scan gantry 20 is relatively linearly moved from a linear movement start point Zs to a linear movement end point Zf as viewed in the z direction when the table 12 is as the reference, and residence times for the scan gantry 20 are provided at the linear movement start point Zs and the linear movement end point Zf to acquire projection data.

At step A1, a scan condition containing a residence time $\tau$ and the like is set based on parameters set by the user. The residence time $\tau$ is assumed to be $\tau 1$ equivalent to one rotation time R of the rotating section 15, for example.

Figure 3:
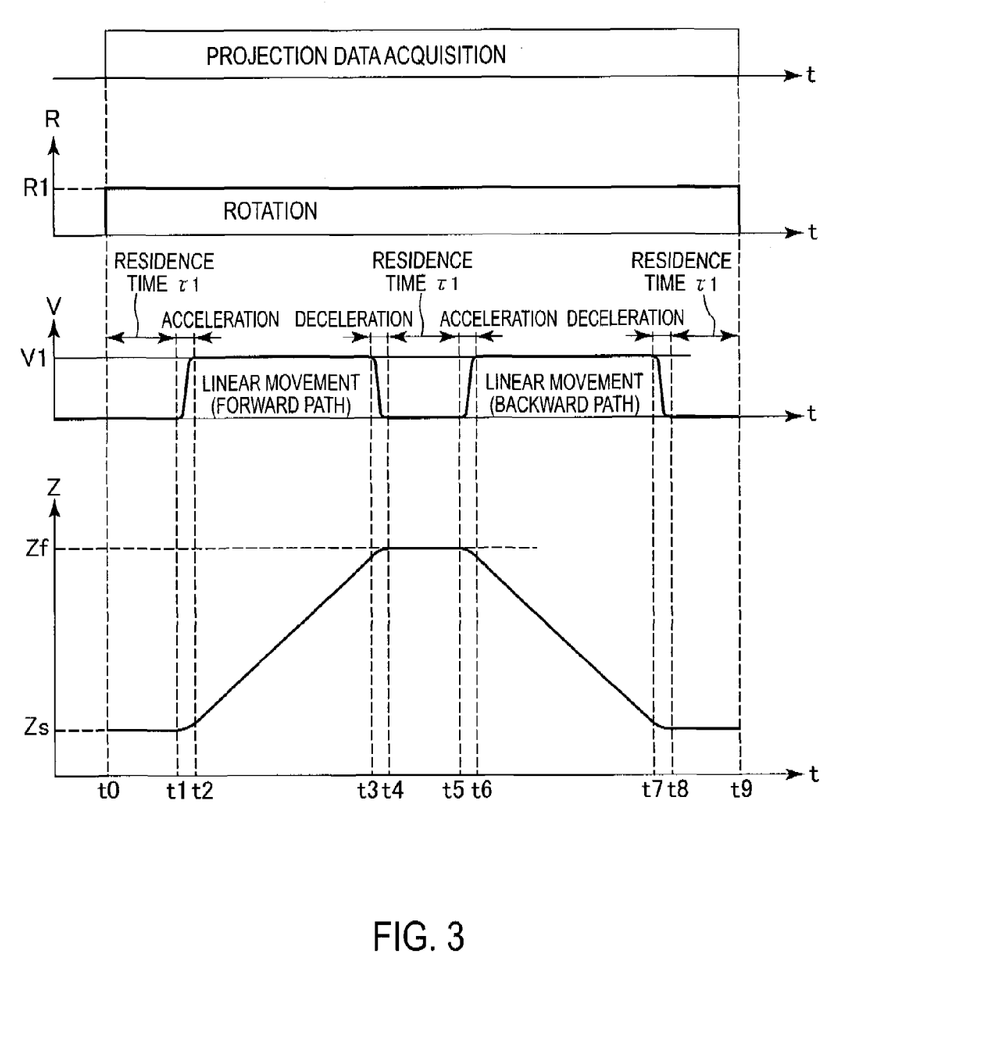
FIG. 3 is a time chart representing "projection data acquisition", "rotation", "linear movement", and "relative positions of X-ray tube and X-ray detector".

At step A2, "projection data acquisition" is started as indicated at a time t0 of FIG. 3, for example.

At step A3, the "rotation" of the rotating section 15 equipped with the X-ray generator and detector system 41 comprised of the X-ray tube 21 and the X-ray detector 24 is started as indicated at the time t0 of FIG. 3, for example.

At step A4, the direction of linear movement of the rotating section 15 to the table 12 is set to the direction of an outward or forward path (+z direction herein).

At step A5, the scan gantry 20 waits by the residence time $\tau 1$ as indicated at the times t0 to t1 of FIG. 3, for example. Namely, the scan gantry 20 is caused to perform only the "rotation" of the rotating section 15, thereby acquiring projection data only during the residence time $\tau 1$ without its linear movement.

At step A6, the "linear movement" of the table 12 is started as indicated at the time t1 of FIG. 3, for example.

At step A7, the table 12 is accelerated as indicated at the times t1 to t2 of FIG. 3, for example. Projection data are acquired even during this period.

At step A8, the table 12 is linearly moved at a constant velocity as indicated at the times t2 to t3 of FIG. 3, for example. Projection data are acquired during this period.

It is determined at step A9 whether the neighborhood of a start or end point of linear movement is reached. If it is determined that the neighborhood thereof is not reached, then the linear movement is caused to continue until its reach. If it is determined that the neighborhood thereof is reached, then the data acquiring process proceeds to step A10.

At step A10, the table 12 is decelerated as indicated at the times t3 to t4 of FIG. 3, for example. Projection data are acquired even during this period.

At step A11, the "linear movement" of the table 12 is completed as indicated at the time t4 of FIG. 3, for example.

At step A12, the scan gantry waits by the residence time $\tau 1$ as indicated at the times t4 to t5 of FIG. 3, for example. Namely, the scan gantry is caused to perform only the "rotation" of the rotating section 15, thereby acquiring projection data only during the residence time $\tau 1$ without its linear movement.

At step A13, the data acquiring process proceeds to step A13 if intended data acquisition is not completed. If it is completed, then the data acquiring process proceeds to step A14.

At step A14, the direction of movement of the table 12 is reversed. Then, the data acquiring process returns to step A6, where the data acquisition is continued. Namely, projection data are acquired while the table 12 is being linearly moved in the direction opposite to the direction at the previous time, with the previous end point being as this start point and the previous start point being as this end point.

At step A15, the "rotation" of the rotating section 15 equipped with the X-ray generator and detector system 41 comprised of the X-ray tube 21 and the X-ray detector 24 is completed as indicated at a time t9 of FIG. 3, for example.

At step A16, the "projection data acquisition" is completed as indicated at the time t9 of FIG. 3, for example.

Figure 4:
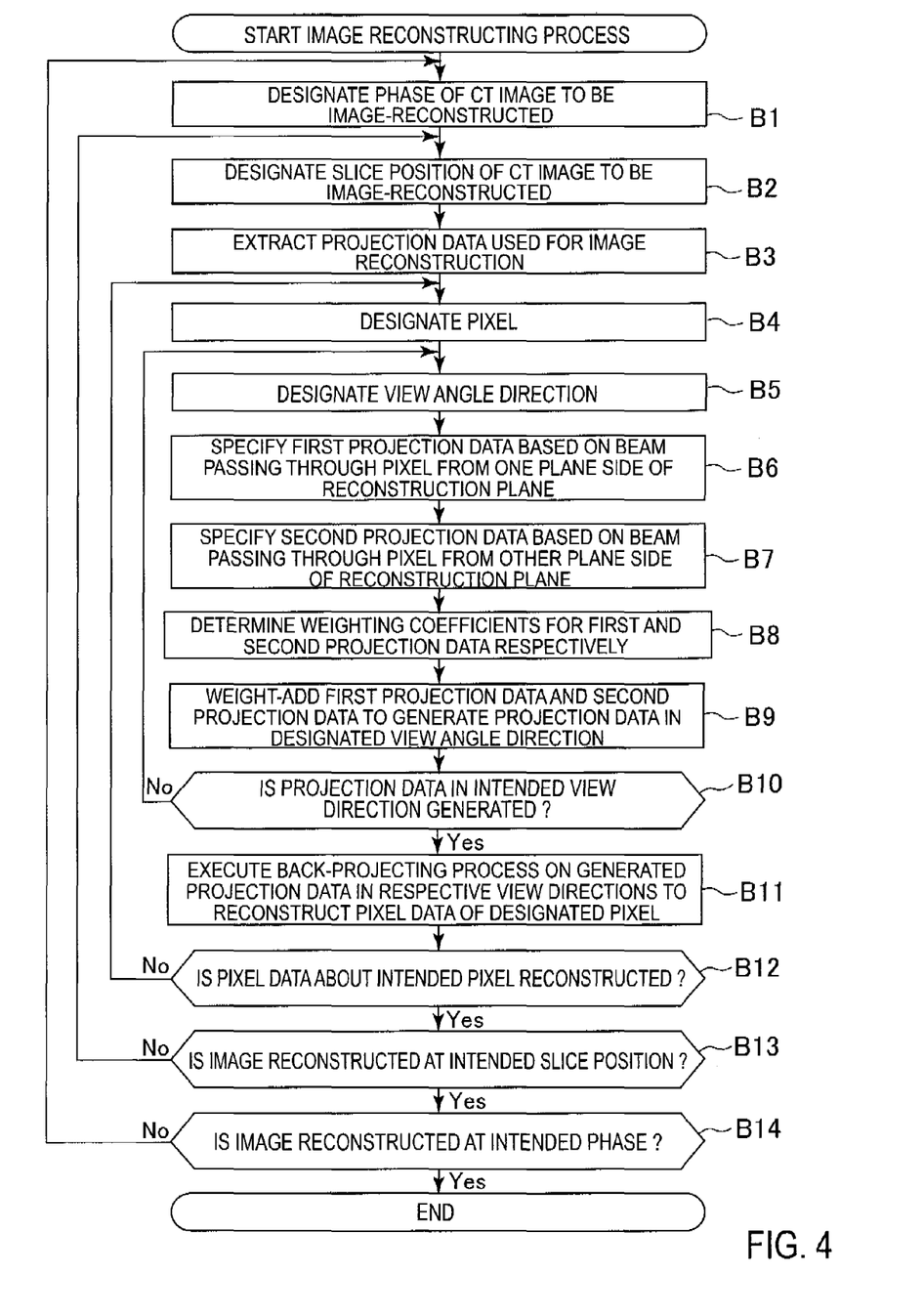
FIG. 4 is a flow diagram showing an image reconstructing process according to the present embodiment.

FIG. 4 is a flow diagram showing an image reconstructing process.

At step B1, a phase Pi of each CT image to be image-reconstructed is designated. Here, the phase Pi means the phase or pass at the time that a helical scan is performed continuously. A first forward path, a first backward path, a second forward path, a second backward path . . . are respectively defined to become a phase P1, a phase P2, a phase P3, a phase P4 . . . . At step B1, the phases are designated one by one in time-series order each time step B1 is executed, for example. Incidentally, the user may set one or plural arbitrary phases or phase's ranges and sequentially designate the phases thereamong.

At step B2, a slice position Zj of each CT image to be image-reconstructed is designated. For example, all regions of an image extension region Rs on the linear movement start point Zs side, a linear movement range Rm and an image extension region Rf on the linear movement end point Zf side are assumed to be a slice position set region. Each time step B2 is executed, slice positions are sequentially designated at predetermined slice intervals in the z direction as viewed from the end of the slice position set region in the slice position set region. Incidentally, the user may set one or plural arbitrary slice positions or slice ranges and sequentially designate the same thereamong.

At step B3, each projection data PDpi,zj used to image-reconstruct the CT image for the slice position Zj at the phase Pi is extracted by, for example, the following method.

A reference view CVpi,zj for the slice position Zj at the phase Pi is first determined. The reference view CVpi,zj is a view for each projection data acquired at a time when a reference position TL of the X-ray generator and detector system 41 coincides with the slice position Zj at the phase Pi. The reference position TL of the X-ray generator and detector system 41 corresponds to, for example, the position of a point where a straight line formed by connecting an X-ray focal point F of the X-ray tube 21 and the center of the X-ray detector 24, and a rotational axis Ic of the X-ray generator and detector system 41 intersect. The reference position TL normally corresponds to the position in the z direction, of the X-ray focal point F. Incidentally, here, the reference position TL of the X-ray generator and detector system 41 is assumed to be a relative position with respect to the subject 40 or the table 12 for convenience.

Of projection data corresponding to plural detector rows in a view range corresponding to a predetermined view angle FR centering on the reference view CVpi,zj, projection data based on an X-ray beam passing through a path extending through a reconstruction plane corresponding to the slice position Zj is next extracted as projection data PDpi,zj. Here, the predetermined view angle FR is equivalent to, for example, $\pi+2\gamma m$ ($\gamma m$=half of fan angle of X-ray beam radiated from X-ray tube 12), $2\pi$, or $2\pi+2\gamma m$.

Specific examples of the projection data extracted by the above method will now be explained using FIG. 5. An upper stage of FIG. 5 typically shows the X-ray tube 21 and X-ray detector 24 at a linear movement start time and a linear movement end time. A lower stage of FIG. 5 typically shows one example of acquired projection data PD for all views. At the lower stage of FIG. 5, the horizontal axis indicates a position Z as viewed in the z direction, and the vertical axis indicates a view number (proportional to the time) View. For every view number, projection data corresponding to a detector width W, i.e., plural detector rows are acquired with the reference position TL relative to the subject 40, of the X-ray generator and detector system 41 being as a center.

As to a slice position Z1 near a linear movement start point Zs at a phase P1, for example, a view CVp1,z1 corresponding to the slice position Z1 at the phase P1 is as a reference view. Of projection data CDp1,z1 in a view range corresponding to a predetermined view angle FR with the reference view taken as the center, projection data based on an X-ray beam that passes through a path extending through a reconstruction plane corresponding to the slice position Z1 is extracted as projection data PDp1,z1.

As to a slice position Z2 lying in the vicinity of the center of a linear movement range Rm at the phase P1, a view CVp1,z2 corresponding to the slice position Z2 at the phase P1 is as a reference view. Of projection data CDp1,z2 in a view range corresponding to a predetermined view angle FR centering on the reference view, projection data based on an X-ray beam that passes through a path extending through the corresponding reconstruction plane corresponding to the slice position Z2 is extracted as projection data PDp1,z2.

At step B4, one pixel P is designated from all pixels on the reconstruction plane RP. Incidentally, when this step B4 is executed after the second time, the corresponding pixel undesignated up to now is designated.

At step B5, one view angle direction θi is designated from respective view angle directions corresponding to view angles necessary to reconstruct pixel data. Incidentally, when this step B5 is executed after the second time, the corresponding view angle direction undesignated up to now is designated.

Figure 6:
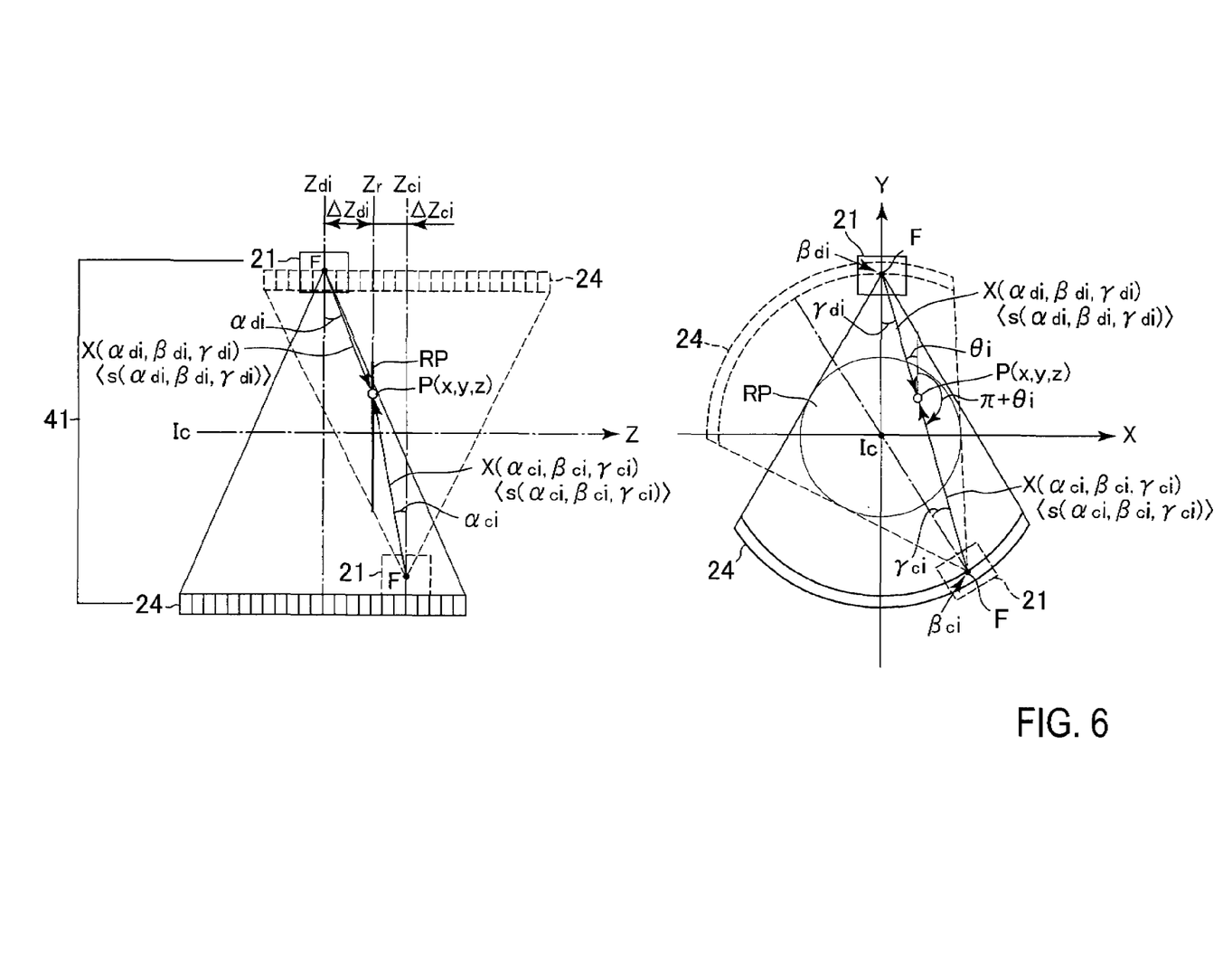
FIG. 6 is a diagram depicting one example of projection data opposite to each other in view angle direction.

At step B6, first projection data s ($\alpha di, \beta di, \gamma di$) at which the angular direction at the time that the corresponding X-ray beam passes through a pixel P or its proximal position from one plane side of the reconstruction plane RP and is projected onto the reconstruction plane RP, is a direction identical or opposite to a view angle direction θi, is specified in projection data PDpi,zj. Here, α indicates a cone angle as viewed from a surface or plane that passes through an X-ray focal point F and a center line in a slice direction, of the X-ray detector 24, β indicates a view angle position of the X-ray focal point F, and γ indicates an angle in a channel direction (direction in which the X-ray beam expands) as viewed from a center line of a fan-shaped X-ray beam radiated from the X-ray tube 21. For example, projection data s ($\alpha di, \beta di, \gamma di$) based on such an X-ray beam X ($\alpha di, \beta di, \gamma di$) as shown in FIG. 6 is specified.

At step B7, second projection data s ($\alpha ci, \beta ci, \gamma ci$) at which the angular direction at the time that the corresponding X-ray beam passes through the pixel P or its proximal position from the other plane side of the reconstruction plane RP and is projected onto the reconstruction plane RP, is a direction identical or opposite to the view angle direction θi, is specified. For example, projection data s ($\alpha ci, \beta ci, \gamma ci$) based on such an X-ray beam X ($\alpha ci, \beta ci, \gamma ci$) as shown in FIG. 6 is specified.

At step B8, weighting coefficients used when the first projection data s ($\alpha di, \beta di, \gamma di$) and the second projection data s ($\alpha ci, \beta ci, \gamma ci$) are weight-added together (subjected to addition with weighting) are determined in accordance with the following equations:

$$\omega(\beta_d i, \gamma_d i) = \frac{\Delta Z_c i + \Delta Z_{offset}(H)}{(\Delta Z_d i + \Delta Z_{offset}(H)) + (\Delta Z_c i + \Delta Z_{offset}(H))} \quad (5)$$

$$\omega(\beta_c i, \gamma_c i) = \frac{\Delta Z_d i + \Delta Z_{offset}(H)}{(\Delta Z_d i + \Delta Z_{offset}(H)) + (\Delta Z_c i + \Delta Z_{offset}(H))} \quad (6)$$

In these equations, $\omega(\beta di, \gamma di)$ indicates a weighting coefficient by which the first projection data s ($\alpha di, \beta di, \gamma di$) is multiplied, and $\omega(\beta ci, \gamma ci)$ indicates a weighting coefficient by which the second projection data s ($\alpha ci, \beta ci, \gamma ci$) is multiplied. ΔZdi indicates a z-direction distance between Zdi corresponding to the reference position TL of the X-ray generator and detector system 41 at the time that the first projection data s ($\alpha di, \beta di, \gamma di$) is acquired, and the reconstruction plane RP. ΔZci indicates a z-direction distance between Zci corresponding to the reference position TL of the X-ray generator and detector system 41 at the time that the second projection data s ($\alpha ci$, $\beta ci$, $\gamma ci$) is acquired, and the reconstruction plane RP. $\Delta Z$offset indicates an offset distance (position predetermined value). Here, it indicates a function having a helical pitch H as a parameter. As the helical pitch H increases, for example, the offset distance $\Delta Z$offset changes so as to become small. A curve indicative of changes in the offset distance $\Delta Z$offset at this time may be a curve that changes continuously or a curve that changes stepwise. When the helical pitch H falls below a constant value or falls above it, the curve may be a curve that changes in such a manner that the offset distance $\Delta Z$offset becomes a constant value.

Figure 7:
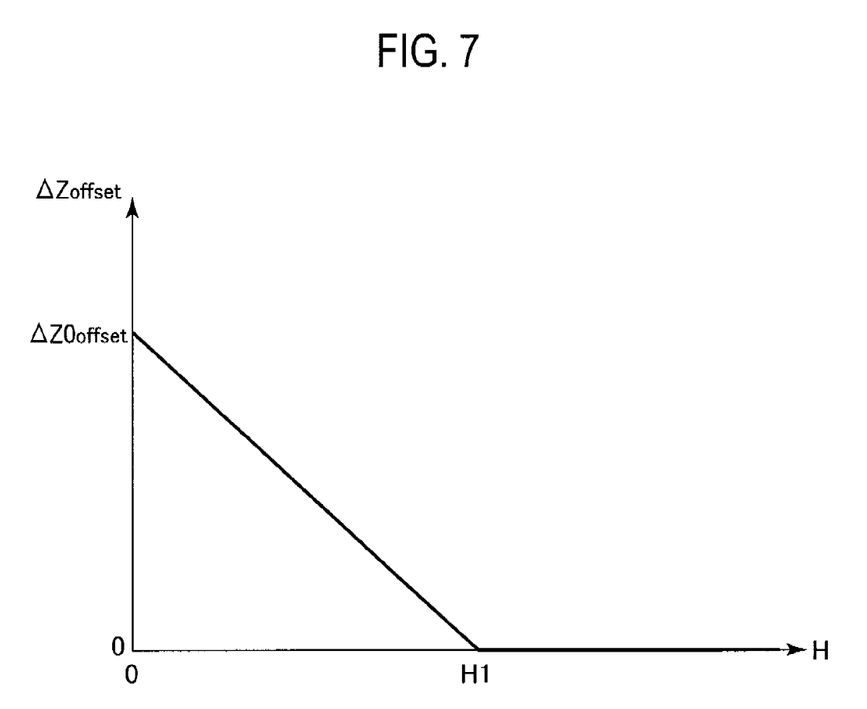
FIG. 7 is a diagram showing one example of a curve of changes in offset distance.

FIG. 7 is a diagram showing one example of a curve indicative of changes in offset distance $\Delta Z$offset. As to the offset distance $\Delta Z$offset, as shown in FIG. 7 for example, the offset distance $\Delta Z$offset changes from $\Delta Z0$offset to 0 (zero) when the helical pitch H changes from 0 (zero) to H1, whereas the offset distance $\Delta Z$offset becomes constant at $\Delta Z$offset=0 when the helical pitch H is larger than H1.

Incidentally, although the range of change in the offset distance $\Delta Z$offset at this time is not limited in particular, for example, a scan width (z-direction width on the rotational axis Ic of an X-ray beam radiated from the X-ray tube 21) W may preferably be changed within a rang of 0 (zero) to 20 d when the width divided by the number of detector rows of the X-ray detector 24 is assumed to be d. Since d=0.625 mm where, for example, the scan width is 40 mm and the number of detector rows is 64, the offset distance $\Delta Z$offset is changed within a range of 0 to 13.5 mm.

The distances $\Delta Zdi$ and $\Delta Zci$ and the helical pitch H are calculated based on information incidental to projection data, i.e., the view angle position $\beta$ of the X-ray focal point F at that time that the projection data are acquired, and the reference position TL of the X-ray generator and detector system 41. The helical pitch H is calculated based on the amount $\Delta\beta$ of change in view angle position of the X-ray focal point F and the amount $\Delta TL$ of change in the reference position TL of the X-ray generator and detector system 41 between the time when the first projection data s ($\alpha di$, $\beta di$, $\gamma di$) is acquired and the time when the second projection data s ($\alpha ci$, $\beta ci$, $\gamma ci$) is acquired, for example.

At step B9, the first projection data s ($\alpha di$, $\beta di$, $\gamma di$) and the second projection data s ($\alpha ci$, $\beta ci$, $\gamma ci$) are weight-added using the weighting coefficients determined at step B8 to thereby generate projection data sdci in a view angle direction $\theta i$, as expressed in the following equation.

$$s_{dc}i = \omega(\beta_d i, \gamma_d i) s(\alpha_d i, \beta_d i, \gamma_d i) + \omega(\beta_c i, \gamma_c i) s(\alpha_c i, \beta_c i, \gamma_c i) \quad (7)$$

It is determined at step B10 whether the generation of projection data in an intended view angle direction is completed. If it is found to have completed, then the image reconstructing process proceeds to step B11. If it is found not to have completed, then the image reconstructing returns to step B5.

At step B11, the generated projection data in each view angle direction $\theta i$ is back-projected to reconstruct the pixel data of the pixel P. Incidentally, backprojection arithmetic processes including weighting, of the step B5 through B11, are as follows if they are collectively expressed in generalized equations. Incidentally, the process of reconstructing actual pixel data is not limited to the above procedure, but various forms are considered therefor depending on algorithms.

$$\tilde{f}(x, y, z) = \frac{\pi}{(\beta_{max} - \beta_{min})} \int_{\beta_{min}}^{\beta_{max}} \frac{R}{\sqrt{(R)^2 + Z^2}} \omega(\beta, \gamma) \tilde{s}(\alpha, \beta, \gamma) d\beta \quad (1)$$

$$\tilde{s}(\alpha, \beta, \gamma) = s(\alpha, \beta, \gamma) \otimes g(\gamma) \quad (2)$$

$$\omega(\beta_d i, \gamma_d i) = \frac{\Delta Z_c i + \Delta Z_{offset}(H)}{(\Delta Z_d i + \Delta Z_{offset}(H)) + (\Delta Z_c i + \Delta Z_{offset}(H))} \quad (5)$$

$$\omega(\beta_c i, \gamma_c i) = \frac{\Delta Z_d i + \Delta Z_{offset}(H)}{(\Delta Z_d i + \Delta Z_{offset}(H)) + (\Delta Z_c i + \Delta Z_{offset}(H))} \quad (6)$$

Description will be made again. In the above equations, f (x, y, z) indicates pixel data of a pixel P (x, y, z) on a reconstruction plane RP, s ($\alpha$, $\beta$, $\gamma$) indicates projection data based on an X-ray beam that passes through the pixel P (x, y, z) or its proximal position on the reconstruction plane RP, g ($\gamma$) indicates a reconstruction function, a symbol $\otimes$ with X being surrounded with $\circ$ indicates a convolution operator, $\alpha$ indicates a cone angle formed as viewed from a plane that passes through the X-ray focal point F and the center line in the slice direction, of the X-ray detector 24, $\beta$ indicates a view angle position of the X-ray focal point F, $\gamma$ indicates an angle in a channel direction as viewed from the center line of a fan-shaped X-ray beam, R indicates the distance from the X-ray focal point F to a rotational center axis Ic, Z indicates a predetermined value that depends on a z coordinate of the pixel P, and $\omega$ ($\beta$, $\gamma$) indicates a weighting coefficient by which projection data s ($\alpha$, $\beta$, $\gamma$) is multiplied. Incidentally, $\beta max-\beta min=\pi+2\gamma m$ in the case of half reconstruction, and $\beta max-\beta min=2\pi$ or $2\pi+2\gamma m$ in the case of full reconstruction.

It is determined at step B12 whether the reconstruction of pixel data about an intended pixel has been completed. If it is found not to have been completed, then the image reconstructing process proceeds to step B4. If it is found to have been completed, then the reconstruction of the CT image of the slice position Zj at the phase Pi is completed and the image reconstructing process proceeds to step B13.

Figure 5:
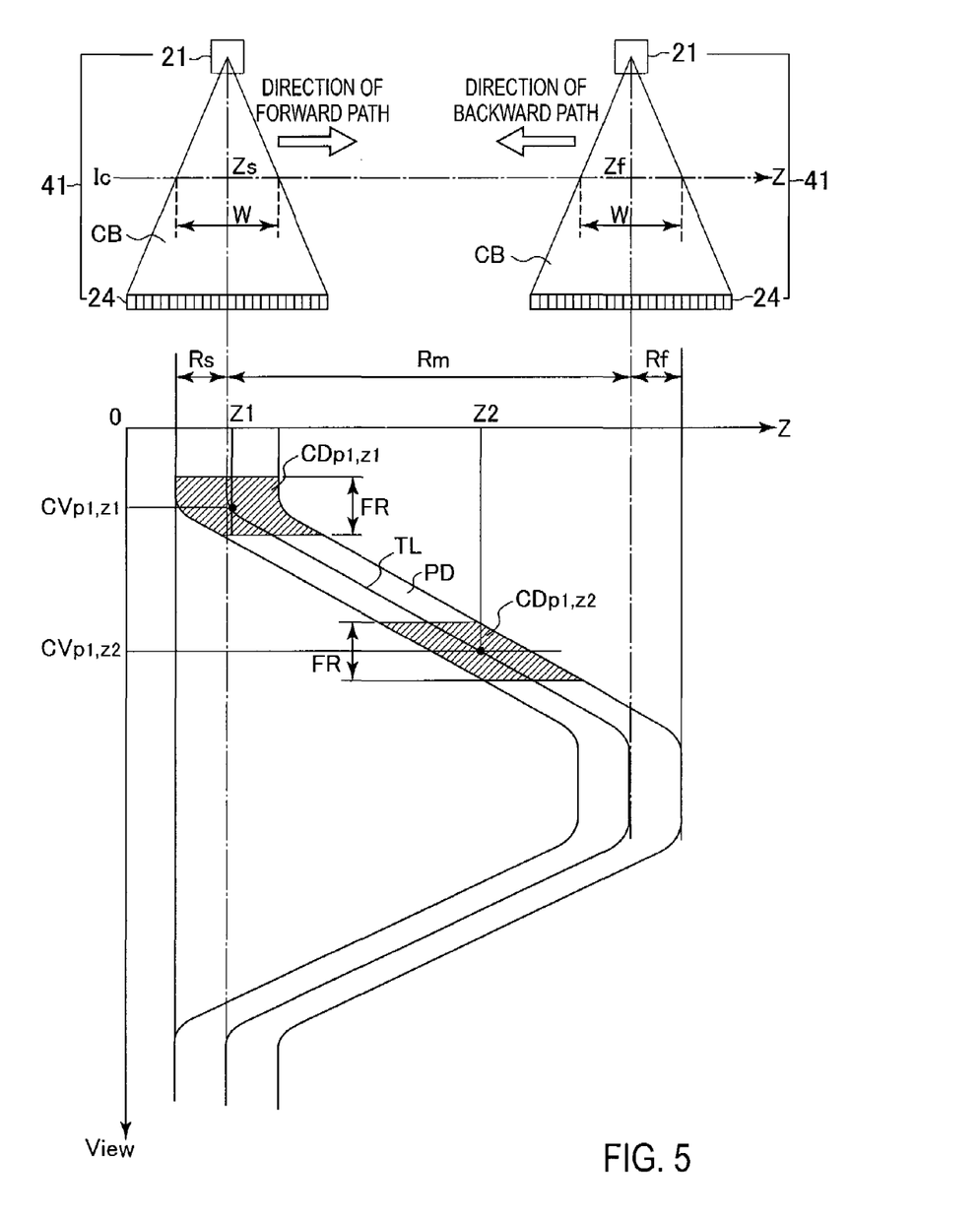
FIG. 5 is a diagram illustrating one example of projection data for image reconstruction extracted in the present embodiment.

When the CT image is image-reconstructed in this way, no disadvantage occurs even in the case in which image reconstruction is performed on the basis of projection data acquired by a helical scan with a small helical pitch, and the like as in the case where the CT image at the slice position Z1 of FIG. 5 is reconstructed, for example.

Figure 8:
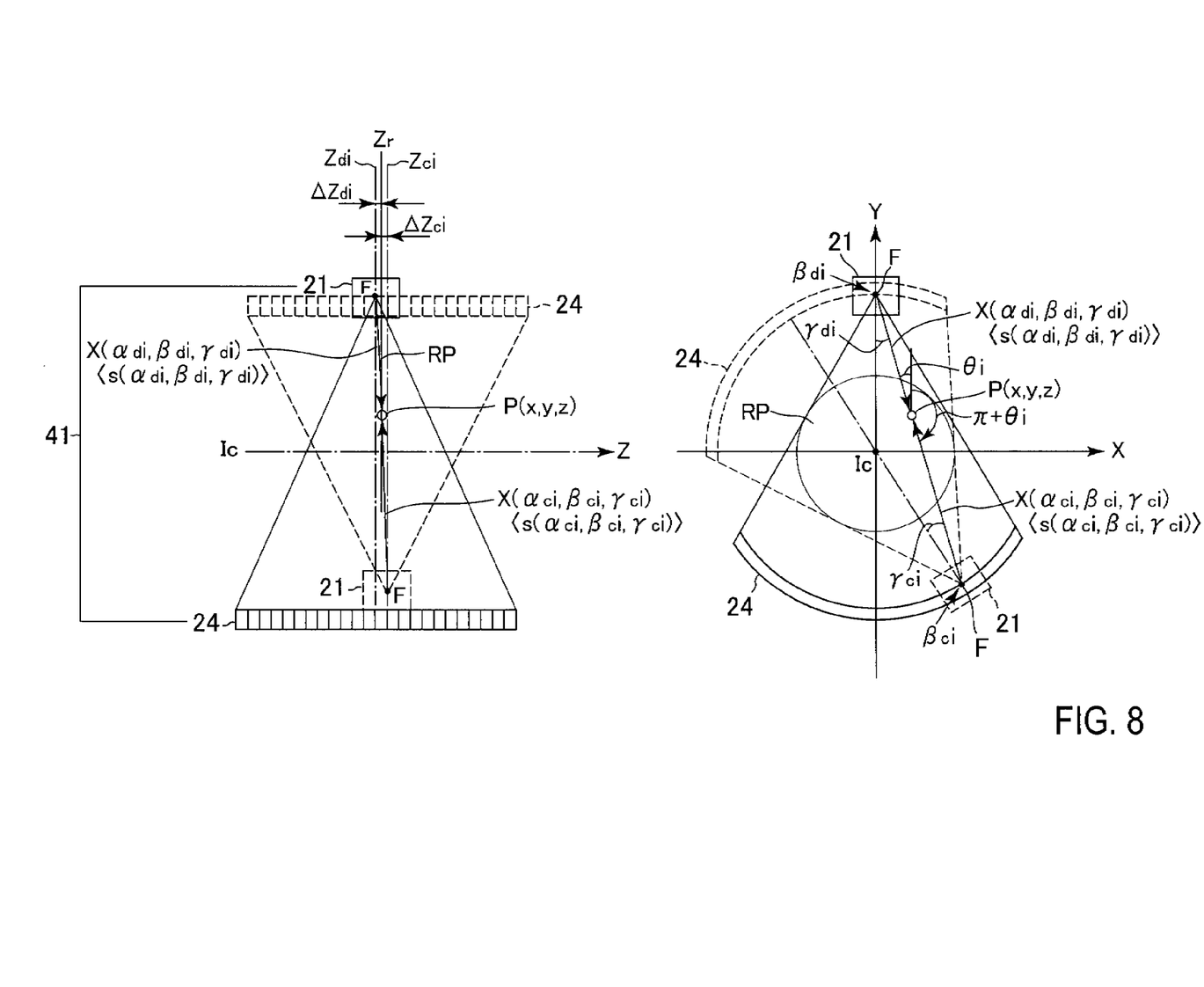
FIG. 8 is a diagram showing one example of projection data opposite to each other in view angle direction where a corresponding X-ray beam comes close to a reconstruction plane.
Figure 9:
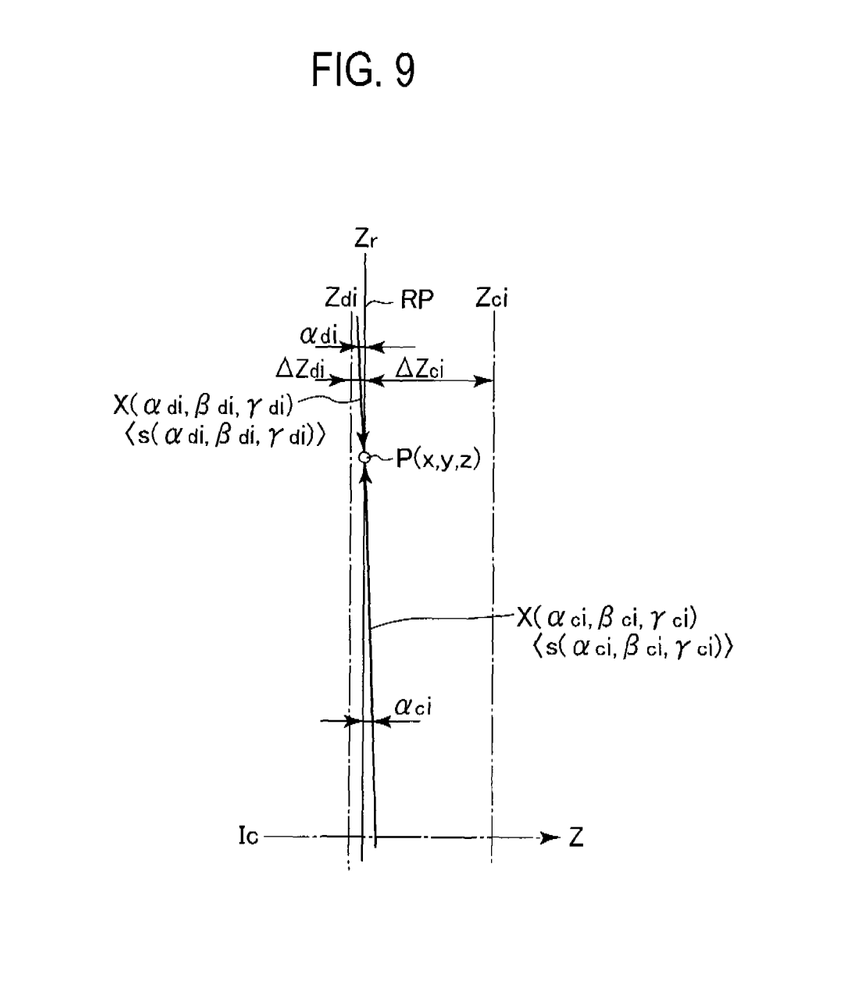
FIG. 9 is an enlarged view of a pixel periphery where the corresponding X-ray beam comes close to the reconstruction plane.

FIG. 8 is a diagram showing first projection data s ($\alpha di$, $\beta di$, $\gamma di$) and second projection data s ($\alpha ci$, $\beta ci$, $\gamma ci$) where both distances $\Delta Zdi$ and $\Delta Zci$ assume a small or minute value near zero, and a large deviation occurs between the distances $\Delta Zdi$ and $\Delta Zci$ as a ratio. FIG. 9 is an enlarged view of the periphery of the pixel P in FIG. 8.

Namely, even though as shown in FIGS. 8 and 9, the distances $\Delta Zdi$ and $\alpha Zci$ both assume the minute value close to zero and the large deviation occurs between $\Delta Zdi$ and $\alpha Zci$ as the ratio, a relatively large weighting coefficient is not assigned to either one of the projection data due to the existence of the offset distance $\Delta Z$offset.

Since the offset distance $\Delta Z$offset changes according to the helical pitch H, a suitable offset distance $\Delta Z$offset corresponding to the magnitude of possibility that the distances $\Delta Zdi$ and $\Delta Zci$ both assume the minute value close to zero can be set. Particularly, since it is considered that the possibility that when the helical pitch H is large, both the distances $\Delta Zdi$ and $\Delta Zci$ will both assume the minute value close to zero becomes low, the setting of decreasing the offset distance $\Delta Z$offset as the helical pitch H becomes large is one preferred example.

Referring back to FIG. 4, it is determined at step B13 whether the image reconstruction of the CT image has been completed at the intended slice position. If it is found not to have been completed, then the image reconstructing process proceeds to step B2. If it is found to have been completed, then the image reconstructing process proceeds to step B14.

It is determined at step B14 whether the image reconstruction of the CT image has been completed at an intended phase. If it is found not to have been completed, then the image reconstructing process proceeds to step B1. If it is found to have been completed, then the image reconstructing process is ended.

Thus, according to the X-ray XT apparatus 100 according to the present embodiment, when the backprojection arithmetic operation including weighting based on the z-direction distance ΔZ between the reconstruction plane of each CT image and the reference position TL of the X-ray generator and detector system 41 corresponding to each view for the projection data is performed to thereby determine the image data of the CT image, the distance obtained by adding the offset distance (positive predetermined value) ΔZoffset to the distance ΔZ is used in the weighting instead of the distance ΔZ. Therefore, even though any of the distances ΔZ corresponding to the respective projection data assumes a minute value, the existence of the offset distance ΔZoffset can prevent a state in which any one of the weighting coefficients (weighting factors) becomes extremely small, and hence the projection data based on the X-ray beam close to the reconstruction plane, of the projection data acquired by the helical scan can reliably be utilized. As a result, the SN ratio (signal-noise ratio) of each CT image can be enhanced and the quality of each CT image can be improved.

When in the conventional weighting-coefficient numerical expressions, the helical pitch approaches zero and the measured distances ΔZc and ΔZd respectively assume zero or a value very close to zero, a state called "division by zero" is reached and hence no appropriate weighting coefficients are calculated. On the other hand, according to the present embodiment, the proper weighting coefficients can be calculated because the existence of the offset distance ΔZoffset included in the weighting-coefficient numerical expressions prevents the state of division by zero.

The measured value of relative position of the X-ray generator and detector system generally varies slightly every measurement in terms of the problem of accuracy of its measurement system. In the conventional numerical expressions of weighting coefficients, when the true value of each distance ΔZ assumes zero or the value very close to zero, the weighting coefficient also becomes instable due to variations in each measure value. Thus, if the times at which the projection data are acquired are different from each other even in the case in which the distances ΔZ are approximately identical in combination theoretically, the calculated weighting coefficients may also vary greatly. Eventually, this leads to the occurrence of an artifact on the reconstructed image. On the other hand, according to the present embodiment, since the existence of the offset distances ΔZoffset contained in the weighting-coefficient equations suppresses the variations in the calculated weighting coefficient, the artifact that occurs on the reconstructed image can be suppressed.

Incidentally, the above embodiment is one example of the present invention and can be changed in various ways.

Although the above embodiment has explained the multi slice X-ray CT apparatus having the multi-row detector as an example, the present invention can similarly be applied even to a single slice X-ray CT apparatus having only a detector row corresponding to one row. In this case, first projection data sd based on an X-ray beam parallel to a reconstruction plane as viewed in a predetermined view angle direction where an X-ray generator and detector system is placed in a first position on one plane side of the reconstruction plane, and second projection data sc based on an X-ray beam parallel to the reconstruction plane as viewed in a view angle direction identical or opposite to the predetermined beam angle direction where the X-ray beam acquiring system is placed in a second position on the other plane side of the reconstruction plane, are subjected to weight adding processing using weighting coefficients with offset distances Zoffset inserted therein.

Although the above embodiment has described as an example where the variable pitch helical scan is carried out, a helical scan whose helical pitch is fixed may be utilized.

Although in the above embodiment, the method of calculating the offset distances Zoffset by the functions each having the helical pitch H as the parameter has been adopted as the method using the offset distances Zoffset each depending on the helical pitch, a method other than it, e.g., a method for forming a table in which each helical pitch and its associated offset distance Zoffset are associated with each other and storing it, and selecting a suitable offset distance Zoffset by reference to this table may be adopted.

Although the offset distance Zoffset depends on the helical pitch in the above embodiment, a fixed value that does not depend on the helical pitch may be used. In either case, a set range of values of offset distances Zoffset is not limited in particular if they are positive values, but they may be set within a range from greater than or equal to d/100 to less than or equal to 30 d using the above width d as a measure. Since d=0.625 mm where, for example, a scan width is 40 mm and the number of detector rows is 64, the offset distance Zoffset may be set within a range from larger than 0 to less than or equal to 18.725 mm.

Although the helical pitch is not limited in the above embodiment, the backprojection arithmetic operation of the projection data used upon the reconstruction of each CT image exhibits a large advantageous effect when the weighting of the projection data acquired where the helical pitch is less than or equal to 0.5 is included. Particularly when the helical pitch is less than or equal to 0.2, it brings out a larger advantageous effect.

In the above embodiment, the weighting coefficients have been determined in consideration of the distance Z (defined by β and γ in terms of each equation) between the X-ray generator and detector system 41 and the reconstruction plane RP at the time that the projection data targeted for the weight adding processing are acquired. Further, however, weighting coefficients having considered the cone angle α of the X-ray beam corresponding to the targeted projection data incident to the reconstruction plane RP may be determined so that the targeted projection data are multiplied by them.

Although the projection data target for the weight adding processing are set as two with respect to one view angle direction in the above embodiment, appropriate weighting coefficients can be determined by a similar method of thinking even if the number of projection data is three or more.

What is claimed is:

1. An image reconstruction method for reconstructing a Computer Tomography (CT) image, said method comprising:
acquiring projection data by a helical scan for performing each scan while relatively linearly moving an X-ray generator and detector system in a direction of a body axis of a subject, wherein the X-ray generator and detector system includes an X-ray tube for radiating X-rays and an X-ray detector having at least one detector row for detecting an X-ray transmitted through the subject; and obtaining image data of the CT image, using projection data lying in a view range including views each corresponding to a time at which a reconstruction plane of the CT image and a reference position of the X-ray generator and detector system coincide with each other in a body-axis direction, by performing a backprojection arithmetic operation including weighting based on a distance in the body-axis direction between the reconstruction plane and the reference position of the X-ray generator and detector system corresponding to the view for the projection data, wherein the weighting is performed based on a distance obtained by adding a predetermined value greater than zero to the distance, in place of the distance.

2. The image reconstruction method according to claim 1, wherein the weighting comprises using weighting coefficients based on a ratio between distances added with the predetermined value at first projection data and second projection data, the first projection data being based on a first X-ray beam passing through a predetermined pixel on the reconstruction plane or its proximal position at a view when the reference position of the X-ray generator and detector system is placed on one plane side of the reconstruction plane, and the second projection data being based on a second X-ray beam passing through the predetermined pixel or its proximal position in a view angle direction substantially identical or opposite to the first projection data at a view when the reference position of the X-ray generator and detector system is placed on the other plane side of the reconstruction plane.

3. The image reconstruction method according to claim 2, wherein the weighting coefficient relative to the first projection data includes a term expressed in the following equation:

$$\frac{\Delta Z_c + \Delta Z_{offset}}{(\Delta Z_d + \Delta Z_{offset}) + (\Delta Z_c + \Delta Z_{offset})},$$

wherein the weighting coefficient relative to the second projection data includes a term expressed in the following equation:

$$\frac{\Delta Z_d + \Delta Z_{offset}}{(\Delta Z_d + \Delta Z_{offset}) + (\Delta Z_c + \Delta Z_{offset})},$$

and wherein $\Delta Z_c$ indicates the distance at the first projection data, $\Delta Z_d$ indicates the distance at the second projection data, and $\Delta Z_{offset}$ indicates the predetermined value.

4. The image reconstruction method according to claim 2, wherein the first X-ray beam passing through a predetermined pixel or its proximal position and the second X-ray beam passing through a predetermined pixel or its proximal position are parallel to the reconstruction plane.

5. The image reconstruction method according to claim 2, wherein the X-ray detector has a plurality of detector rows, and wherein the first X-ray beam passing through a predetermined pixel or its proximal position and the second X-ray beam passing through a predetermined pixel or its proximal position pass through the reconstruction plane.

6. The image reconstruction method according to claim 1, wherein the predetermined value becomes small as a helical pitch becomes large.

7. The image reconstruction method according to claim 6, wherein the predetermined value changes according to a helical pitch at a variable pitch helical scan at which the helical pitch changes while the helical scan is being performed.

8. The image reconstruction method according to claim 1, wherein the backprojection arithmetic operation includes weighting of projection data acquired where the helical pitch is 0.5 or less.

9. The image reconstruction method according to claim 1, wherein the predetermined value falls within a range from greater than or equal to d/100 to less than or equal to 30 d when a width obtained by dividing a width in the body-axis direction, of an X-ray beam radiated from the X-ray tube by the number of the detector rows is defined as d.

10. The image reconstruction method according to claim 1, wherein the view range corresponds to a view angle of π+fan angle of an X-ray beam radiated from the X-ray tube, 2π, or a 2π+view angle of the fan angle.

11. The image reconstruction method according to claim 1, wherein the reference position of the X-ray generator and detector system corresponds to a position of a point where a straight line formed by connecting an X-ray focal point of the X-ray tube and the center of the X-ray detector, and a rotational axis of the X-ray generator and detector system intersect.

12. An X-ray Computed Tomography (CT) apparatus comprising:

an X-ray generator;

a detector system;

a data acquiring device configured to acquire projection data by a helical scan for performing each scan while relatively linearly moving the X-ray generator and the detector system in a direction of a body axis of a subject, wherein said X-ray generator and detector system comprises an X-ray tube configured to radiate X-rays and an X-ray detector comprising at least one detector row configured to detect X-rays transmitted through the subject; and an image reconstructing device configured to reconstruct a CT image using the acquired projection data, wherein said image reconstructing device is configured to obtain image data of the CT image, using projection data lying in a view range including views each corresponding to a time at which a reconstruction plane of the CT image and a reference position of said X-ray generator and detector system coincide with each other in the body-axis direction, by performing a backprojection arithmetic operation including weighting based on a distance in the body-axis direction between the reconstruction plane and the reference position of said X-ray generator and detector system, corresponding to the view for the projection data, and wherein the weighting is performed based on a distance obtained by adding a predetermined value greater than zero to the distance, in place of the distance.

13. The X-ray CT apparatus according to claim 12, wherein said image reconstructing device is configured to use, for the weighting, weighting coefficients based on a ratio between distances added with the predetermined value at first projection data and second projection data, the first projection data being based on a first X-ray beam passing through a predetermined pixel on the reconstruction plane or its proximal position at a view when the reference position of said X-ray generator and detector system is placed on one plane side of the reconstruction plane, and the second projection data being based on a second X-ray beam passing through the predetermined pixel or its proximal position in a view angle direction substantially identical or opposite to the first projection data at a view when the reference position of said X-ray generator and detector system is placed on the other plane side of the reconstruction plane.

14. The X-ray CT apparatus according to claim 13, wherein a first weighting coefficient relative to the first projection data includes a term expressed in the following equation:

$$\frac{\Delta Z_c + \Delta Z_{offset}}{(\Delta Z_d + \Delta Z_{offset}) + (\Delta Z_c + \Delta Z_{offset})},$$

wherein a second weighting coefficient relative to the second projection data includes a term expressed in the following equation:

$$\frac{\Delta Z_d + \Delta Z_{offset}}{(\Delta Z_d + \Delta Z_{offset}) + (\Delta Z_c + \Delta Z_{offset})},$$

and wherein $\Delta Z_c$ indicates the distance at the first projection data, $\Delta Z_d$ indicates the distance at the second projection data, and $\Delta Z_{offset}$ indicates the predetermined value.

15. The X-ray CT apparatus according to claim 13, wherein the first X-ray beam passing through a predetermined pixel or its proximal position and the second X-ray beam passing through a predetermined pixel or its proximal position are parallel to the reconstruction plane.

16. The X-ray CT apparatus according to claim 13, wherein said X-ray detector comprises a plurality of detector rows, and wherein the first X-ray beam passing through a predetermined pixel or its proximal position and the second X-ray beam passing through a predetermined pixel or its proximal position pass through the reconstruction plane.

17. The X-ray CT apparatus according to claim 12, wherein the predetermined value becomes small as a helical pitch becomes large.

18. The X-ray CT apparatus according to claim 17, wherein the predetermined value changes according to a helical pitch at a variable pitch helical scan at which the helical pitch changes while the helical scan is being performed.

19. The X-ray CT apparatus according to claim 12, wherein the backprojection arithmetic operation includes weighting of projection data acquired where the helical pitch is 0.5 or less.

20. The X-ray CT apparatus according to claim 12, wherein the predetermined value falls within a range from greater than or equal to d/100 to less than or equal to 30d when a width obtained by dividing a width in the body-axis direction, of an X-ray beam radiated from said X-ray tube by a number of said at least detector row is defined as d.

21. The X-ray CT apparatus according to claim 12, wherein the view range corresponds to a view angle of π+fan angle of an X-ray beam radiated from said X-ray tube, 2π, or a 2π+view angle of the fan angle.

22. The X-ray CT apparatus according to claim 12, wherein the reference position of said X-ray generator and detector system corresponds to a position of a point where a straight line formed by connecting an X-ray focal point of said X-ray tube and the center of said X-ray detector, and a rotational axis of said X-ray generator and detector system intersect.

* * * * *